United States Patent [19]
Schreinemakers

[11] Patent Number: 5,163,841
[45] Date of Patent: Nov. 17, 1992

[54] CORRECTING ARTICULATION DEFECT IN DENTATE HUMAN JAW

[76] Inventor: Josephus Schreinemakers, Oranje Nassaulaan 12, 6026 Maarheeze, Netherlands

[21] Appl. No.: 682,737

[22] Filed: Apr. 9, 1991

Related U.S. Application Data

[62] Division of Ser. No. 471,211, Jan. 26, 1990, Pat. No. 5,018,972.

Foreign Application Priority Data

Feb. 5, 1989 [DE] Fed. Rep. of Germany ....... 3903391

[51] Int. Cl.$^5$ ..................... A61C 19/04; A61C 11/00; A61C 5/00
[52] U.S. Cl. ........................ 433/72; 433/56; 433/68; 433/215
[58] Field of Search ............... 433/54, 55, 56, 59, 433/68, 72, 73

References Cited

U.S. PATENT DOCUMENTS

| | | | |
|---|---|---|---|
| 2,239,294 | 4/1941 | Opotow | 433/73 |
| 3,200,497 | 8/1965 | Goodfriend | 433/56 |
| 3,577,855 | 5/1971 | Baum | 433/73 |
| 3,763,565 | 10/1973 | Faust et al. | 433/72 |
| 4,096,637 | 6/1978 | Stade | 433/73 |
| 4,576,576 | 3/1986 | Spanko | 433/72 |
| 4,654,005 | 3/1987 | Woelfel | 433/72 |
| 4,762,490 | 8/1988 | Ludwigs | 433/56 |
| 4,906,186 | 3/1990 | France | 433/72 |

Primary Examiner—Gene Mancene
Assistant Examiner—Cindy A. Cherichetti
Attorney, Agent, or Firm—Herbert Dubno; Andrew Wilford

[57] ABSTRACT

A model of a maxilla is marked with the location of the patient's lip line and with the location of the patient's ear-nose plane. Then the incisor portion of the model is shaped to have a lower edge lying on the location of the lip line. A calibration plate having a posterior ridge engaging the tuberosity portion of the model, an anterior part engaging the shaped incisor portion of the model, and sides formed with slots aligned with the molar portions of the model is then positioned on the model. The plate extends substantially parallel to the ear-nose plane from shaped front of the model. The slots are filled around the molar portions of the model with wax and a mold fork is fitted flat to the underside of the calibration plate underneath the slots with the compound adhering to the mold fork. Thereafter the fork and the compound are separated from the plate and model and are fitted to the patient. The relative angular orientation between the fork and the patient's ear-nose plane is ascertained and if the fork and plane are not substantially parallel more compound and a different calibration plate is tried, but if the fork and plane are substantially parallel another plate having the same dimensions and ridge height as the plate used with the parallel-lying fork but not formed with slot is selected from the set of calibration plates. Finally the model is ground down using the unslotted plate as a template.

1 Claim, 3 Drawing Sheets

CORRECTING ARTICULATION DEFECT IN DENTATE HUMAN JAW

CROSS REFERENCE TO RELATED APPLICATION

This application is a division of copending patent application Ser. No. 07/471,211 filed 26 Jan. 1990, now U.S. Pat. No. 5,018,972.

FIELD OF THE INVENTION

The present invention relates to the correction of a joint or articulation defect in a dentate human jaw. More particularly this invention concerns tools for making such an adjustment.

BACKGROUND OF THE INVENTION

In a standard procedure for correcting a bite articulation defect in a dentate human jaw, impressions are taken of the maxilla and mandible, that is the upper and lower jaws, and positive models are prepared. Each model has portions corresponding not only to the front incisor, canine, and side molar regions of the patient's teeth, but also portions corresponding to the maxillary and mandibular tuberosities, that is the bony protuberances behind the third molars. A calibration plate is then used to work on the models thus produced in order to reset the so-called articulation or chewing plane.

An articulation defect is defined relative to this joint plane which itself is defined in the front by the lip line of the patient and in the rear by the jaw joint. This joint plane should be parallel to a plane defined by the centers of the ear holes in the rear and the bottom edges of the sides of the nose in the front.

Misalignments of the joint plane can result from teeth having been removed from the upper or lower jaws and the teeth in the opposing jaw shifting complementarily out. In the long run such a joint misalignment can result in considerable problems. Thus it is standard to fit crowns or bridges to patients who have or might develop such a joint-plane misalignment.

Normally the existence of a joint-plane misalignment is determined by visual examination of the model. It is also known to use a so-called articulator in which the model is mounted to try out solutions to the joint problem. Calibration plates are used which follow the uneven contours defined by the prominences of the teeth of the model.

The known method which uses an articulator nonetheless makes it very difficult to transfer any measurements to the patient accurately. Due to the inability to transfer these measurements to the natural teeth of the patient it is relatively difficult to guarantee good long-term results. This is particularly true when the patient is being fitted with a bridge, crown, or the like and it is necessary to determine whether there is any articulation defect and correct it. Typically marking paper is used to leave traces where the teeth meet, but this procedure is not highly accurate.

OBJECTS OF THE INVENTION

It is therefore an object of the present invention to provide improved tools for preparing for correcting an articulation defect in a dentate human jaw.

Another object is the provision of such improved tools for preparing for correcting an articulation defect in a dentate human jaw which overcome the above-given disadvantages, that is which are simple and highly accurate.

SUMMARY OF THE INVENTION

A preparation method for correcting a bite-articulation defect in a human patient according to the invention comprises first making a positive model of a dentate human maxilla including the tuberosity thereof and of the respective mandible. Thus each model has portions corresponding to the patient's incisors, molars, and tuberosities. The front of the maxilla model is marked with the location of the patient's lip line and on the back it is marked with the location of the patient's ear-nose plane. Then the incisor portion of the maxilla model is shaped to have a lower edge lying on the location of the lip line. A calibration plate having a posterior ridge engaging the tuberosity portion of the maxilla model, an anterior part engaging the shaped incisor portion of the maxilla model, and sides formed with slots aligned with the molar portions of the maxilla model is then positioned on the maxilla model The plate is selected from a set of plates of different ridge heights such that the slotted plate extends substantially parallel to the ear-nose plane from the shaped front of the maxilla model. The side slots are filled around the molar portions of the maxilla model with mold-making compound, typically wax, and a mold fork is fitted flat to the underside of the calibration plate underneath the slots with the compound adhering to the mold fork. Thereafter the fork and the compound are separated from the plate and maxilla model and are fitted to the patient. The relative angular orientation between the fork and the patient's ear-nose plane is ascertained and if the fork and plane are not substantially parallel more compound and a different calibration plate is tried, but if the fork and plane are substantially parallel another plate having the same dimensions and ridge height as the plate used with the parallel-lying fork but not formed with a slot is selected from the set of calibration plates. Finally the maxilla model is ground down using the unslotted plate as a template.

Subsequently the teeth of the patient can be ground down or built up to correspond to the model, thereby eliminating the articulation defect. It is also possible after grinding down the model to insert between the mandible and maxilla models a synthetic-resin pattern which can subsequently be inserted into the mouth of the patient for use in correcting the teeth therein. It is understood that in accordance with this invention corrective grinding is carried out on the side teeth, that is the molars and premolars. Furthermore the steps of this invention are repeated with the mandible model after being carried out on the maxilla model.

A kit for carrying out the method of this invention therefore comprises a set of slotted calibration plates of different ridge heights and a set of unslotted calibration plates of different ridge heights and each of dimensions corresponding to a respective one of the slotted plates. The slotted and unslotted plates of each set according to this invention are graduated in accordance with jaw size and the ridge heights vary from plate to plate within the set by between 1 mm and 2 mm, with the shortest ridge 1 mm high and the tallest one 12 mm high. The slotted plates are set in the model parallel to the ear-nose plane as described above after the model is marked. Then the slots are filled with wax and the bite-mold fork is fitted to the plate. This fork with the impression is inserted in the patients to take the occlusal surfaces of the natural teeth so as to verify parallelism with ear-nose plane which, as mentioned above, runs parallel to the articulation plane.

Several ways can be employed to ensure that the calibration plate is parallel to the ear-nose plane on the upper- or lower-jaw model. The above-mentioned mold fork can be used in a method where so much compound is packed into the slots that it flows out and also fills this fork, or even is inserted thereinto by means of the fork which itself has parallel upper and lower surfaces and lies flatly against the planar bottom face of the calibration plate. Then when the fork is fitted to the patient it will run parallel to the ear-nose plane if the calibration plate itself was properly positioned. Once thus determined the ear-nose plane can be marked with a pencil on the model, or at least a plane parallel thereto can be marked on the model. It is also possible to try out different calibration plates until the right one for the ear-nose plane is determined.

The method according to this invention therefore introduces into the determination of a joint-plane error a new reference point, namely the desired orientation of the calibration plate which is determined by grinding down the teeth on the model. Thus the invention recognizes that on the one hand supporting the calibration plate at one end on the tuberosity regions of the models by the plate ridge and at the other end on at the lip line produces the ideal articulation plane for the patient. This allows one to ascertain relatively easily just where articulation defects lie so that same can be eliminated, either by grinding down or building up the teeth.

Thus according to the invention the slotted and unslotted calibration plates have a curved upper surface whose curvature closely corresponds to the curvature of the upper prominences of the occlusal surfaces of the molars and premolars. An imaginary forward extension of this surface corresponds to the lip line regardless of the position of the front teeth. This means that the lip line serves as an orientation point for the front end of the calibration plate. A known law states that the ear-nose plane, the so-called Campers plane, extends parallel to the articulation plane. The curvature of the calibration plate and of the articulation plane are identical, both having in the posterior region a distinct curvature and in the region of the second and third molars an increased upward curvature. This latter curvature in the region of the second and third molars is disregarded in determining the parallelism between the articulation plane and the ear-nose plane. This disregarding is possible in that lateral edges on the rear side of the calibration plates extend in the sagittal region before the premolars and first rollers straight back. The position of this straight portion is according to this invention transferred to the mold fork. Subsequently the mouth of the patient is used to test if indeed the mold fork does extend parallel to the ear-nose plane.

The distance between the highest point of the tuberosities and the occlusal surface of the nearest molar lies between 1 mm and 12 mm, depending on the patient. Thus for each individual a matched pair of slotted and unslotted plates, that is each having the same dimensions and ridge heights, allows the ridge to lie in the middle of the tuberosities with the plate just touching the occlusal surface of the rearmost molar and the outer edge of the front incisor.

DESCRIPTION OF THE DRAWING

The above and other objects, features, and advantages will become more readily apparent from the following, reference being made to the accompanying drawing in which.

SPECIFIC DESCRIPTION

Figure 1:
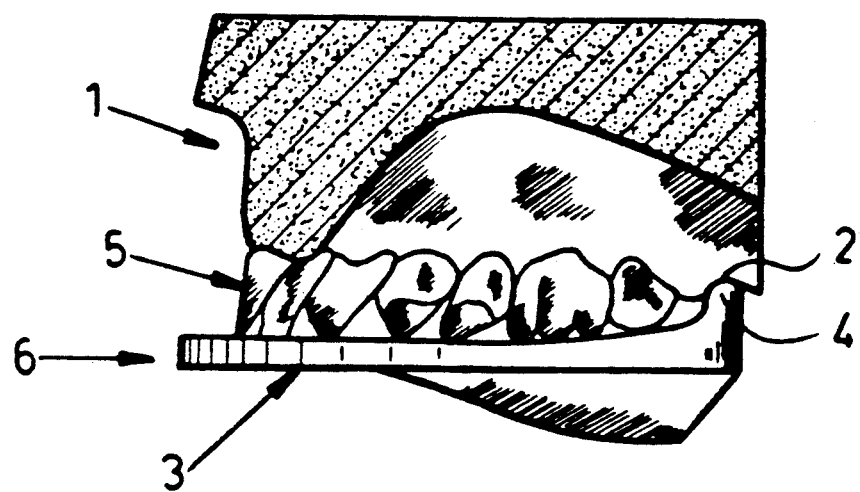
FIG. 1 is a vertical section through a maxilla model fitted with an unslotted calibration plate according to this invention.
Figure 2:
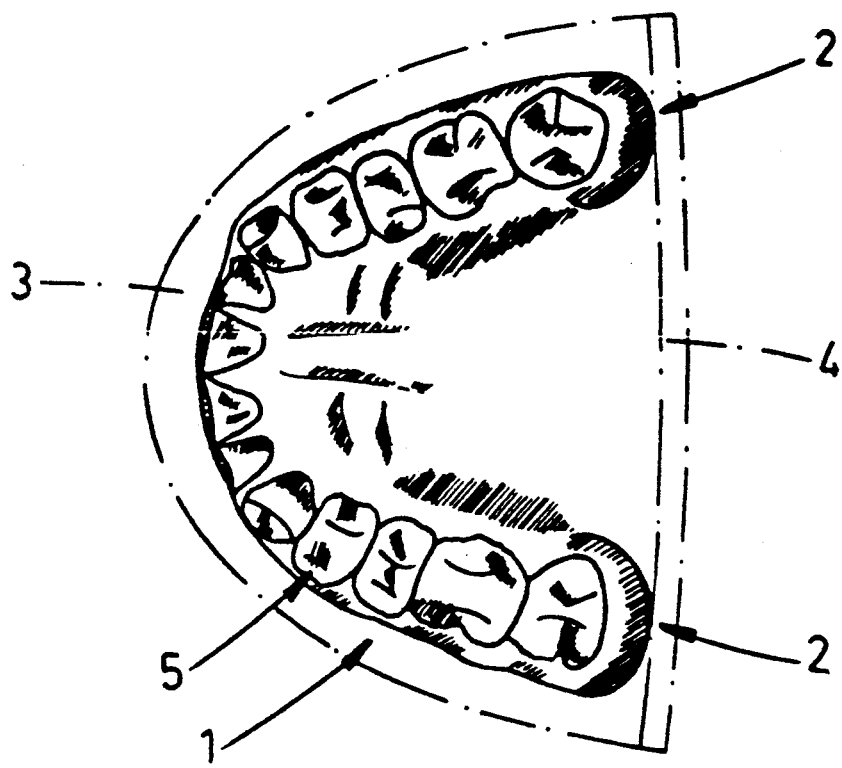
FIG. 2 is a bottom view of the model according to FIG. 1.

As seen in FIG. 1 a positive model 1 of a dentate human maxilla, which is made as is normal by taking a negative impression with wax or the like and then filling the impression with plaster or the like, has a region 2 conforming to the maxillary tuberosity. An unslotted calibration plate 3 has a rear ridge 4 engaging the tuberosities 2 and a front portion engaging upward against the lower edge of the front incisors 5, which lower edge has been ground down or built up to lie level with the patient's lip line 6.

Figure 3:
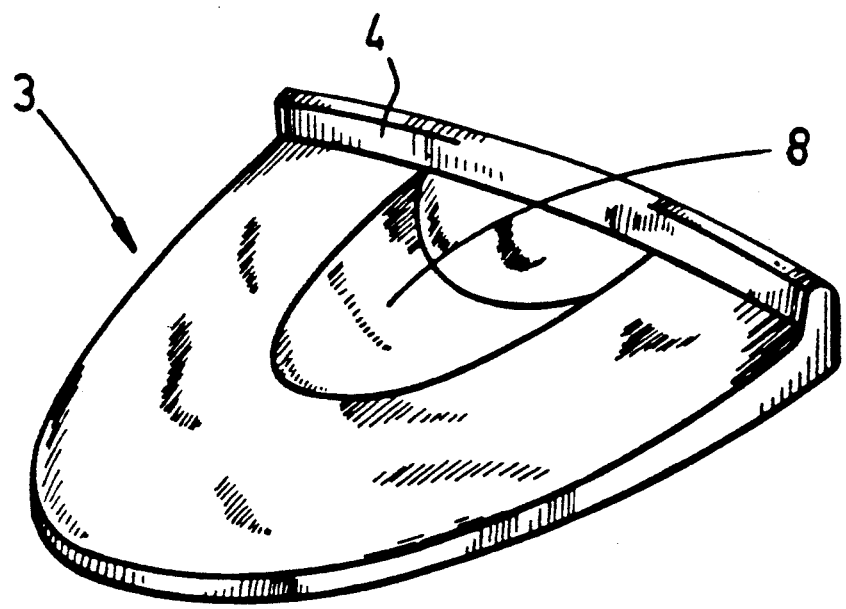
FIGS. 3 and 4 are perspective views of a pair of matched upper-jaw calibration plates.

FIG. 3 shows how the plate 3 is generally flat with a downwardly directed and upwardly concave dome 8. This plate 3 belongs to a set of such plates wherein the height of the ridge 4 increases by 1 mm to 2 mm between succeeding plates in the series.

Figure 4:
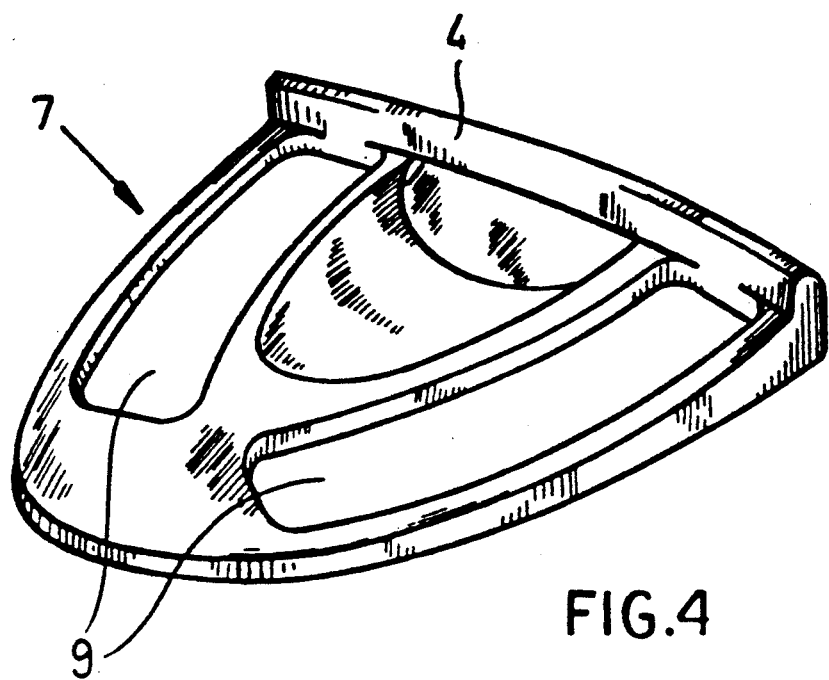
Figure 5:
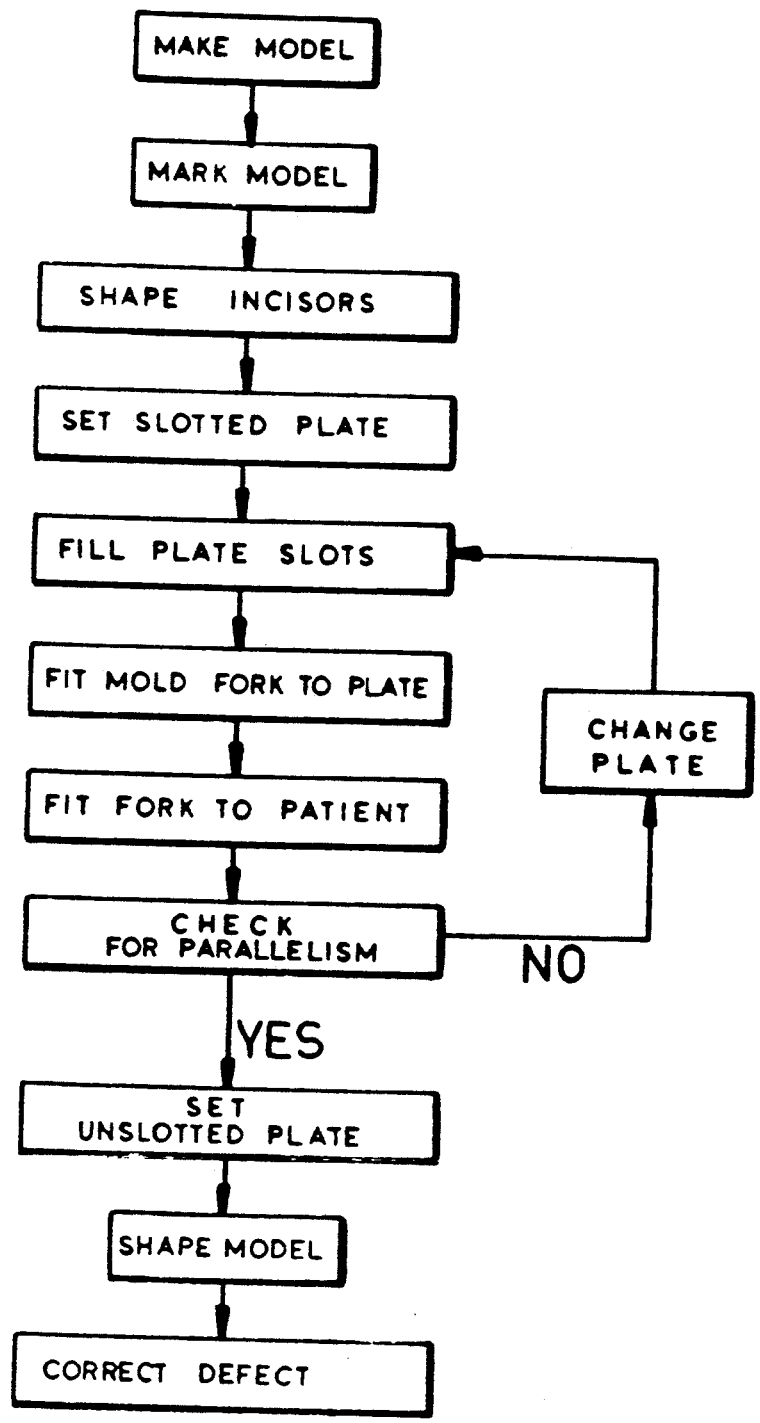
FIG. 5 is a block diagram describing the steps of the method of this invention.

In FIG. 4 a plate 7 is shown having an identical such ridge 4, but formed with slots 9 through which the premolars and molars can extend. In all other respects this plate 7 is identical to the plate 3 of FIG. 3.

I claim:

1. A kit for preparing for a correction of a bite-articulation correction of a human patient, the kit comprising
a set of slotted calibration plates of different ridge heights each of a size sufficient to substantially fill the patient's mouth with the respective slots in lateral molar/premolar regions of the patient's mouth and the respective ridge engaging the tuberosity portion of the patient's mouth, the slotted plates of each set being graduated in accordance with jaw size with the ridge heights varying from plate to plate within the set by between 1 mm and 2 mm; and
a set of unslotted calibration plates of different ridge heights and each of dimensions and overall shape corresponding substantially identically to a respective one of the slotted plates, the unslotted plates of each set being graduated in accordance with jaw size with the ridge heights varying from plate to plate within the set by between 1 mm and 2 mm.

* * * * *